United States Patent
Bok et al.

[11] Patent Number: 6,133,241
[45] Date of Patent: *Oct. 17, 2000

[54] BIOFLAVONOIDS AS PLASMA HIGH DENSITY LIPOPROTEIN LEVEL INCREASING AGENT

[75] Inventors: Song-Hae Bok; Tae-Sook Jeong, both of Daejeon; Surk-Sik Moon, Chungcheongnam-do; Yong-Kook Kwon, Daejeon; Byung-Hwa Hyun, Daejeon; Chul-Ho Lee, Daejeon; Yang-Kyu Choi, Daejeon; Myung-Sook Choi, Daegu; Sung-Gyu Kim, Daejeon; Og-Sung Moon, Daejeon; Sae-Bom Lee, Daejeon; Eun-Sook Lee, Daejeon; Byung-Tae Ahn, Chungcheongbuk-do, all of Rep. of Korea

[73] Assignee: Korea Institute of Science & Technology, Seoul, Rep. of Korea

[*] Notice: This patent is subject to a terminal disclaimer.

[21] Appl. No.: 09/177,448

[22] Filed: Oct. 22, 1998

[51] Int. Cl.$^7$ .................................................. A61K 31/70

[52] U.S. Cl. .......................... 514/27; 514/456; 424/195.1

[58] Field of Search ................... 514/27, 456; 424/195.1

[56] References Cited

U.S. PATENT DOCUMENTS

| | | | |
|---|---|---|---|
| 3,876,777 | 4/1975 | Horowitz et al. | 424/180 |
| 4,496,548 | 1/1985 | Moldowan et al. | 514/27 |
| 5,763,414 | 6/1998 | Bok et al. | 514/27 |

Primary Examiner—Elli Peselev
Attorney, Agent, or Firm—Anderson Kill & Olick, PC

[57] ABSTRACT

A method for increasing the plasma high density lipoprotein (HDL) level in a mammal comprises administering a bioflavonoid of formula(I) or plant extract containing same thereto:

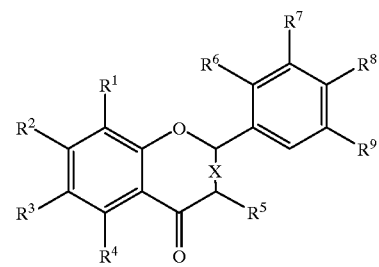

(I)

wherein, $R^1$, $R^2$, $R^3$, $R^4$, $R^5$, $R^6$, $R^7$, $R^8$ and $R^9$ are each independently hydrogen; a hydroxy group; a $C_{1-9}$ alkoxy group optionally substituted with one or more substituents selected from the group consisting of a hydroxy, $C_{1-5}$ alkoxy, aryloxy, and phenyl group substituted with 1 to 3 substituents selected from the group consisting of a hydroxy, alkoxy, aryloxy, halogen, nitro and amido group; a $C_{5-9}$ cycloalkyloxy group substituted with 1 to 3 substituents selected from the group consisting of a hydroxy, alkoxy, aryloxy, halogen, nitro and amido group; a $C_{5-9}$ cycloalkylcarbonyloxy group substituted with 1 to 3 substituents selected from the group consisting of a hydroxy, alkoxy, aryloxy, halogen, nitro and amido group; a $C_{2-10}$ or $C_{16-18}$ acyloxy group optionally substituted with one or more substituents selected from the group consisting of a hydroxy, $C_{1-5}$ alkoxy, aryloxy, and phenyl group substituted with 1 to 3 substituents selected from the group consisting of a hydroxy, alkoxy, aryloxy, halogen and nitro group; a rutinosyl group; or a rhaminosyl group; and X is a single or double bond.

11 Claims, No Drawings

BIOFLAVONOIDS AS PLASMA HIGH DENSITY LIPOPROTEIN LEVEL INCREASING AGENT

FIELD OF THE INVENTION

The present invention relates to a method for increasing the plasma high density lipoprotein(HDL) level in a mammal by administering a bioflavonoid thereto.

BACKGROUND OF THE INVENTION

In recent years, coronary cardio-circulary diseases, e.g., atherosclerosis and hypercholesterolemia, have increasingly become a major cause of deaths. It has been reported that an elevated plasma cholesterol level causes the deposition of fat, macrophages and foam cells on the wall of blood vessels, such deposit leading to plaque formation and then to atherosclerosis(Ross, R., *Nature*, 362, 801–809(1993)).

Specifically, it has been reported that a high ratio of plasma low density lipoproteins(LDL) to total cholesterol causes atherosclerosis very easily, while plasma HDL-cholesterol is beneficial to health. A recent study exhibited that increase in the plasma HDL level is inversely related to the occurrence of a heart disease(Barter P. J., Rye K. A., *High density lipoproteins and coronary heart disease, Atherosclerosis* 121:1–12(1996)).

Lamarche et al. have found that a combination of hypertriglyceridemia, a low plasma HDL level, an abdominal fatness and the like is a major risk factor causing atherosclerosis, thereby discovering that a low plasma HDL level is also an important risk factor of atherosclerosis (Lamarche B., Lewis G. F., *Atherosclerosis prevention for the next decade: risk assessment beyond low density lipoprotein cholesterol, Can. J. Cardiol.* 14:841–851(1998)). In addition, Lacko et al. have verified that plasma HDL has anti-inflammatory and anti-atherosclerosis activities(Lacko A. G., Miller N. E., *International symposium on the role of HDL in disease prevention: report on a meeting, J. Lipid Research* 38:1267–1273(1997)).

Therefore, numerous efforts have been made to develop medicines to increase the plasma HDL level; and, as a result, a pharmaceutical composition for increasing the plasma HDL level has been reported(U.S. Pat. No. 5,783,600, issued on Jul. 21, 1998). However, said composition comprises chemically synthesized compounds as an active ingredient, which may induce adverse side effects in a human body in terms of toxicity or pharmaceutical activities.

The present inventors have endeavored to develop a non-toxic plasma HDL level increasing agent from natural materials, and, as a result, have discovered that bioflavonoids isolated from edible plants are effective to increase the plasma HDL level.

Generally, various bioflavonoids, such as those listed in Table I, are present in the citrus peel(Horowitz, R. M. et al., *J. Org. Chem.*, 25, 2183–2187(1960)). Hesperidin is the major bioflavonoid component found in orange, lemon and tangerine; naringin represents the major bioflavonoid component in grapefruit; and naringin and hesperidin are present in citron in nearly equal amounts.

TABLE I

| Citrus fruit | Bioflavonoids |
| --- | --- |
| Grapefruit | apigenin, dihydrokaempferol, eriodictyol, hesperetin, hesperidin, isorhamnetin, isosakuranetin, neohesperidin, poncirin, quercetin, rutin |
| Lemon | apigenin, apigenin 7-rutinoside, chrysoeriol, diosmin, eriocitrin, hesperidin, isorhamnetin, limocitrin limocitrol, luteolin 7-rutinoside, naringin, neohesperidin, poncirin, quercetin |
| Orange | auranetin, hesperidin, isosakuranetin 7-rutinoside, naringin, neohesperidin, nobiletin, rutin, sinensetin, tangeretin, vitexin |
| Tangerine | hesperidin, nobiletin, tangeretin |

It has been reported that the bioflavonoids isolated from citrus peel have an anti-oxidative, anti-cancer, anti-viral and blood-pressure lowering activities(Saija, A., et al., *Free Radical Biol. Med.*, 19, 481–486(1995); Matsubara, Y., et al., *Japan Organic Synthesis Chem. Association Journal*, 52, 318–327(1994, Mar.); Galati, E. M., et al., *Farmaco.*, 51(3), 219–221(1996, Mar.); Felicia, V., et al., Nutr. Cancer, 26, 167–181(1996); EP 0352147 A2(1990. 1. 24); and Kaul, T. N., et al., *J. Med. Viol.*, 15, 71–75(1985)).

However, bioflavonoids have never been reported to have plasma HDL level increasing activity.

SUMMARY OF THE INVENTION

Accordingly, it is a primary object of the present invention to provide a method for increasing the plasma HDL level in a mammal.

In accordance with the present invention, there is provided a method for increasing the plasma HDL level in a mammal which comprises administering an effective amount of a bioflavonoid of formula(I) or a plant extract containing same thereto:

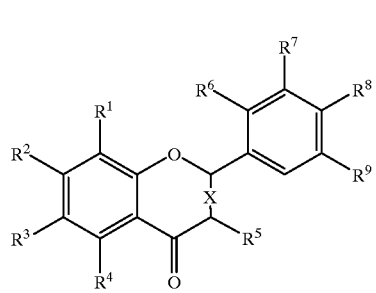

(I)

wherein
$R^1$, $R^2$, $R^3$, $R^4$, $R^5$, $R^6$, $R^7$, $R^8$ and $R^9$ are each independently hydrogen; a hydroxy group; a $C_{1-9}$ alkoxy group optionally substituted with one or more substituents selected from the group consisting of a hydroxy, $C_{1-5}$ alkoxy, aryloxy, and phenyl group substituted with 1 to 3 substituents selected from the group consisting of a hydroxy, alkoxy, aryloxy, halogen, nitro and amido group; a $C_{5-9}$ cycloalkyloxy group substituted with 1 to 3 substituents selected from the group consisting of a hydroxy, alkoxy, aryloxy, halogen, nitro and amido group; a $C_{5-9}$ cycloalkylcarbonyloxy group substituted with 1 to 3 substituents selected from the group consisting of a hydroxy, alkoxy, aryloxy, halogen, nitro and amido group; a $C_{2-10}$ or $C_{16-18}$ acyloxy group optionally substituted with one or more substituents selected from the group consisting of a hydroxy, $C_{1-5}$ alkoxy, aryloxy, and phenyl group substituted with 1 to 3 substituents selected from the group consisting of a hydroxy, alkoxy, aryloxy, halogen and nitro group; a rutinosyl group; or a rhaminosyl group; and X is a single or double bond.

DETAILED DESCRIPTION OF THE INVENTION

Among the bioflavonoids of the present invention, preferred are those of formula(I) wherein: $R^1$ is H; $R^2$ is OH, a rutinosyl or rhaminosyl group; $R^3$ is H; $R^4$ is OH; $R^5$ is H, OH or a rutinosyl group; $R^6$ is H; $R^7$ is H or OH; $R^8$ is OH or $OCH_3$; and $R^9$ is H.

Particularly preferred bioflavonoids of formula(I) of the present invention are shown in Table II.

Alternatively, buckwheat seeds may be allowed to stand overnight in an aqueous solution of $Ca(OH)_2$ or NaOH, and then crude rutin precipitates may be collected after neutralization. Further, dry powders of buckwheat seeds, leaves, stems and flowers may also be used. Generally, the content of rutin in leaves and stems of buckwheat is about 0.6% and that in buckwheat flower is about 3%.

The citrus which can be used in the present invention may be tangerine, orange, lemon, grapefruit and citron. It is preferable to use the peel of citrus fruits uncontaminated by chemical pesticides. The citrus peel extract may be prepared by any of the conventional methods using water or other suitable solvents such as aqueous alcohol, $Ca(OH)_2$ and NaOH.

On the other hand, neohesperidin dihydrochalcone ($C_{28}H_{36}O_{15}$) of formula(II), which can be easily derived from naringin and has a 1,000 to 1,500 fold higher sweetness than sucrose, may also be used for increasing the plasma HDL level:

TABLE II

| | $R^1$ | $R^2$ | $R^3$ | $R^4$ | $R^5$ | $R^6$ | $R^7$ | $R^8$ | $R^9$ | X |
|---|---|---|---|---|---|---|---|---|---|---|
| Eridictyol | H | OH | H | OH | H | H | OH | OH | H | single bond |
| Hesperidin | H | ORut | H | OH | H | H | OH | $OCH_3$ | H | single bond |
| Hesperetin | H | OH | H | OH | H | H | OH | $OCH_3$ | H | single bond |
| Naringin | H | ORha | H | OH | H | H | H | OH | H | single bond |
| Naringenin | H | OH | H | OH | H | H | H | OH | H | single bond |
| Apigenin | H | OH | H | OH | H | H | H | OH | H | double bond |
| Luteolin | H | OH | H | OH | H | H | OH | OH | H | double bond |
| Diosmin | H | ORut | H | OH | H | H | OH | $OCH_3$ | H | double bond |
| Kaemferol | H | OH | H | OH | OH | H | H | OH | H | double bond |
| Quercetin | H | OH | H | OH | OH | H | OH | OH | H | double bond |
| Rutin | H | OH | H | OH | ORut | H | OH | OH | H | double bond | note)
ORut: Rutinosyl group
ORha: Rhaminosyl group

The bioflavonoids of the present invention may be extracted from various plants including vegetables such as lettus and onion, fruits such as citrus fruit, and grains such as buckwheat, or synthesized in accordance with the conventional process described by Zemplen, Bognar in *Ber.*, 1043(1943) and Seka, Prosche, *Monatsh.*, 69, 284(1936). For example, rutin and quercetin may be extracted from buckwheat by using a suitable solvent such as water or aqueous alcohol under a high temperature and pressure.

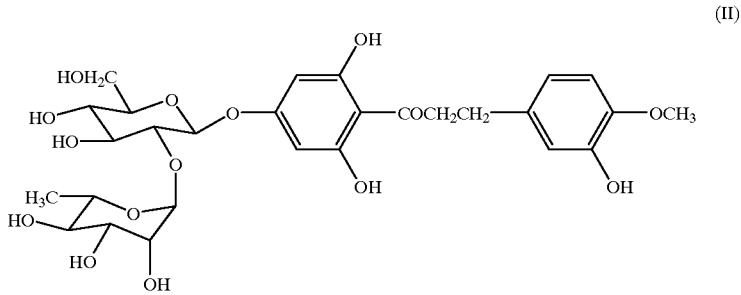

(II)

Bioflavonoids of formula(I) and (II) start to exert a plasma HDL level increasing effect at a dose of only 0.1 mg/kg/day, the effect increasing with the dose thereof.

Moreover, in spite of their potent efficacies, the bioflavonoid and plant extract containing same show little toxicity or mitogenicity in tests using mice. More specifically, naringin, naringenin, hesperidin, hesperetin, diosmin, neohesperidin dihydrochalcone, quercetin or rutin exhibits no toxicity when it is orally administered to a mouse at a dose of 1,000 mg/kg. Further, the bioflavonoid or the citrus peel extract exerts no adverse effects on the liver function.

The present invention also provides a pharmaceutical composition for increasing the plasma HDL level, which comprise the bioflavonoid or the plant extract containing same as an active ingredient and pharmaceutically acceptable excipients, carriers or diluents.

A pharmaceutical formulation may be prepared in accordance with any of the conventional procedures. In preparing the formulation, the active ingredient is preferably admixed or diluted with a carrier, or enclosed within a carrier which may be in the form of a capsule, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a mammal by employing any of the procedures well known in the art.

The pharmaceutical composition of the present invention can be administered via various routes including oral, transdermal, subcutaneous, intravenous and intramuscular introduction. In case of human, a typical daily dose of the bioflavonoid may range from about 0.1 to 500 mg/kg body weight, preferably 0.5 to 100 mg/kg body weight, and can be administered in a single dose or in divided doses.

However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

Moreover, the bioflavonoid or the plant extract containing same in the form of an additive or a dietary supplement can be incorporated in foods or beverages for the purpose of increasing the plasma HDL level. The foods or beverages may include meats; juices such as a vegetable juice(e.g., carrot juice and tomato juice) and a fruit juice(e.g., orange juice, grape juice, pineapple juice, apple juice and banana juice); chocolates; snacks; confectionery; pizza; foods made from cereal flour such as breads, cakes, crackers, cookies, biscuits, noodles and the likes; gums; dairy products such as milk, cheese, yogurt and ice creams; soups; broths; pastes; ketchups and sauces; teas; alcoholic beverages; carbonated beverages such as Coca-Cola® and Pepsi-Cola®; vitamin complexes; and various health foods.

In this case, the content of the bioflavonoid in a food or beverage may range from 0.01 to 50% by weight, preferably 0.05 to 10% by weight. In particular, the beverage according to the present invention may comprise 200 to 10,000 mg of the bioflavonoid per 1000 ml of the beverage. In case of plant powder, the content thereof in a food or beverage may range from 0.5 to 30% by weight.

As described above, a bioflavonoid or a plant extract containing same can be used as an effective, non-toxic pharmaceutical agent for increasing the plasma HDL level.

The following Examples are intended to further illustrate the present invention without limiting its scope.

Further, percentages given below for solid in solid mixture, liquid in liquid, and solid in liquid are on a wt/wt, vol/vol and wt/vol basis, respectively, and all the reactions were carried out at room temperature, unless specifically indicated otherwise.

EXAMPLE 1

Toxicity of Orally Administered Rutin 12 seven-week-old specific pathogen-free ICR mice, six female mice each weighing about 25 to 29 g and six male mice each weighing about 34 to 38 g, were bred under an environment of $22\pm1°$ C., $55\pm5$ % relative humidity and 12L/12D photoperiod. Fodder(Cheiljedang Co., mouse and rat fodder) and water were sterilized and fed to the mice.

Rutin(Sigma Chemical Co., St. Louis, Mo., U.S.A.) was dissolved in 0.5% Tween 80 to a concentration of 100 mg/ml, and the solution was orally administered to the mice in an amount of 0.2 ml per 20 g of mouse body weight. The solution was administered once and the mice were observed for 10 days for signs of adverse effects or death according to the following schedule: 1, 4, 8, and 12 hours after the administration and, every 12 hours thereafter. The weight changes of the mice were recorded every day to examine the effect of rutin. Further, on the 10th day, the mice were sacrificed and the internal organs were visually examined.

All the mice were alive at day 10 and rutin showed no toxicity at a dose of 1,000 mg/kg. The autopsy revealed that the mice did not develop any pathological abnormality, and no weight loss was observed during the 10 day test period. Accordingly, it was concluded that rutin is not toxic when orally administered to an animal.

EXAMPLE 2

Administration of Bioflavonoids to an Animal-(1)

(Step 1) Animal Test 40 three-week-old Sprague-Dawley rats (Taihan laboratory animal center, Korea) each weighing about 90 to 110 g were evenly divided into four dietary groups by a randomized block design. The rats of the four groups were fed with four different high-cholesterol diets, i.e., AIN-76 laboratory animal diet(ICN Biochemicals, Cleveland, Ohio, U.S.A.) containing 1% cholesterol(Control group), 1% cholesterol plus 0.1% hesperetin(Hesperetin group), 1% cholesterol plus 0.1% naringin(Naringin group) and 1% cholesterol plus 16.7% citrus peel extract(Citrus peel extract group), respectively. The compositions of diets fed to the four groups are shown in Table III.

TABLE III

| Dietary group Ingredients | Control group | Hesperetin group | Naringin group | Citrus peel extract[*4] group |
|---|---|---|---|---|
| Casein | 20 | 20 | 20 | 20 |
| D,L-methionine | 0.3 | 0.3 | 0.3 | 0.3 |
| Corn starch | 15 | 15 | 15 | 15 |
| Sucrose | 49 | 48.9 | 48.9 | 32.3 |
| Cellulose powder[*1] | 5 | 5 | 5 | 5 |
| Mineral mixture[*1] | 3.5 | 3.5 | 3.5 | 3.5 |
| Vitamin mixture[*1] | 1 | 1 | 1 | 1 |
| Choline bitartrate | 0.2 | 0.2 | 0.2 | 0.2 |

TABLE III-continued

| Dietary group Ingredients | Control group | Hesperetin group | Naringin group | Citrus peel extract*[4] group |
|---|---|---|---|---|
| Corn oil | 5 | 5 | 5 | 5 |
| Cholesterol | 1 | 1 | 1 | 1 |
| Hesperetin*[2] | — | 0.1 | — | — |
| Naringin*[2] | — | — | 0.1 | — |
| Citrus peel extract*[3] | — | — | — | 16.7 |
| Total | 100 | 100 | 100 | 100 |

*[1]Purchased from TEKLAD Premier Co. (Madison, WI, U.S.A.).
*[2]Purchased from Sigma Chemical Company (St. Louis, Mo., U.S.A.)
*[3]Prepared by extracting the tangerin peel in 30% ethanol during 3 hours, followed by concentrating the resulting extract by vacuum
*[4]0.1% hesperidin equivalent The rats were allowed to feed freely on the specified diet together with water for eight weeks, the ingestion amount was recorded daily and the rats were weighed every 7 days, and then the record was analyzed. All rats showed a normal growth rate and there was observed no significant difference among the three groups in terms of the feed ingestion amount and the weight gain.

(Step 2) Blood Analysis

The effect of administering bioflavonoids to rats on the plasma cholesterol was determined as follows.

Blood samples were taken from the rats of the four dietary groups and plasma HDL fractions were separated therefrom by using the method of adding a HDL-cholesterol reagent (Chiron Diagnostics Co., USA) containing dextran-sulfate to the plasma from the blood sample in a ratio of reagent:plasma=1:10, reacting the mixture in an incubator for 5 minutes and, then, centrifuging the resulting mixture on a speed of 2,500 rpm for 10 minutes(Stein, E. A., et al., *Clin. Chem.*, 24:1112–1115(1978); Finley, P. R., et al., *Clin. Chem.*, 24:931–933(1978); Warnick, G. R., et al., *Clin. Chem.*, 28:1379–1388(1982)). Total cholesterol and HDL-cholesterol levels were determined by using a Blood Chemical Analyzer(Ciba Corning 550 Express, USA). The result is shown in Table IV, wherein the ratio of HDL-cholesterol/total-cholesterol level increased by 27, 52 and 67% in the hesperetin, naringin and citrus peel extract groups, respectively, as compared with that of the control group.

TABLE IV

| Group Lipids Conc. | Control group | Hespere-tin group | Naringin group | Citrus peel extract group |
|---|---|---|---|---|
| Total-C (mg/dl) | 147.11 ± 11 | 125.1 ± 16.1 | 100.8 ± 16.1 | 94.5 ± 12 |
| HDL-C (mg/dl) | 22.2 ± 2.1 | 25.7 ± 1.5 | 24.0 ± 1.5 | 24.8 ± 1.0 |
| HDL-C (%) Total-C | 15.7 ± 1.6 | 20.0 ± 1.9 | 23.9 ± 3.1 | 26.2 ± 7.5 |

* Total-C: Total-cholesterol
* HDL-C: HDL-cholesterol

EXAMPLE 3

Administration of Bioflavonoids to an Animal-(2)

(Step 1) Animal Test 34 four-week-old male Sprague-Dawley rats(Taihan laboratory animal center, Korea) each weighing about 110 to 130 g were evenly divided into four dietary groups by a randomized block design. The rats of the four groups were fed with four different diets, i.e., test diet 5799M-B(PMI, U.S.A.) containing 1% cholesterol and 20% lard(Control group); 1% cholesterol and 20% lard plus 0.1% diosmin (Diosmin group); 1% cholesterol and 20% lard plus 0.05% neohesperidin dihydrochalcone(Neohesperidin group); and 1% cholesterol and 20% lard plus 0.1% rutin(Rutin group), respectively. Test diet 5799M-B comprises 21% vitamin free casein, 15% sucrose, 3% cellulose, 2% vitamin mixture, 5% mineral mixture, 0.15% D,L-methionine, 0.5% sodium cholate, 32.15% dextrin, 20% lard, 0.2% choline chloride and 1% cholesterol. 8 or 9 rats were allotted to each group and diosmin, neohesperidin dihydrochalcone and rutin were purchased from Sigma Chemical Company(St. Louis, Mo., U.S.A.). The rats were bred for 6 weeks while being allowed free access to the diets and water.

(Step 2) Blood Analysis

The effect of administering bioflavonoids to rats on the plasma cholesterol was determined as follows.

Blood samples were taken from the rats and total cholesterol and HDL-cholesterol levels were determined in accordance with the same procedure in (Step 2) of Example 2. The result is shown in Table V.

TABLE V

| Group Lipids Conc. | Control group | Diosmin group | Neohesperidin group | Rutin group |
|---|---|---|---|---|
| Total-C (mg/dl) | 690 | 503 | 336 | 373 |
| HDL-C (mg/dl) | 70 ± 19 | 131 ± 59 | 180 ± 90 | 216 ± 11 |
| HDL-C (%) Total-C | 10 | 26 | 53 | 58 |

* Total-C: Total-cholesterol
* HDL-C: Total-cholesterol

As can be seen from Table V, bioflavonoids of the present invention increase the plasma HDL remarkably in an animal and, thereby, suppressing the onset of cardio-circulary diseases.

EXAMPLE 4

Administration of Bioflavonoids to Man

Two men in their fifties were treated with daily oral dosage of 10 mg/kg of naringin and hesperidin, respectively, for 2 months. The plasma HDL level was determined before and after the administration. The result is shown in Table VI.

TABLE VI

| | Average plasma HDL level (mg/dl) | | |
|---|---|---|---|
| Group | Before Administration | After 2 months | Increase rate (%) |
| Naringin | 51 | 60 | 18 |
| Hesperidin | 47 | 56 | 19 |

Consequently, naringin and hesperidin increased the plasma HDL level by 18% and 19%, respectively, in comparison to that before the administration.

EXAMPLE 5

HDL increasing agent

Hard gelatin capsules were prepared using the following ingredients:

|  | Quantity (mg/capsule) |
| --- | --- |
| Active ingredient (bioflavonoids) | 200 |
| Vitamin C | 50 |
| Lactose (carrier) | 150 |
| Total | 400 mg |

EXAMPLE 6

Foods containing Bioflavonoids (1) Preparation of tomato ketchup and sauce

Naringin was added to a tomato ketchup or sauce in an amount ranging from 0.01 to 50 wt % to obtain a health-improving tomato ketchup or sauce.

(2) Preparation of wheat flour foods

Rutin was added to a wheat flour in an amount ranging from 0.01 to 50 wt % and breads, cakes, cookies, crackers and noodles were prepared by using the mixture to obtain health-improving foods.

(3) Preparation of soups and gravies

Quercetin was added to soups or gravies in an amount ranging from 0.01 to 50 wt % to obtain a health-improving soups or gravies.

(4) Preparation of ground beef

Diosmin was added to ground beef in an amount ranging from 0.01 to 50 wt % to obtain a health-improving ground beef.

(5) Preparation of dairy product

Rutin or Quercetin was added to milk in an amount ranging from 0.01 to 50 wt % to obtain a health-improving milk.

Especially, in case of cheese preparation, rutin or quercetin was added to the coagulated milk protein, and in case of yogurt preparation, rutin or quercetin was added to the coagulated milk protein after the fermentation.

EXAMPLE 7

Beverages containing Bioflavonoids (1) Preparation of vegetable juice 200 to 10,000 mg of hesperidin was added to 1000 ml of a tomato or carrot juice to obtain a health-improving vegetable juice.

(2) Preparation of fruit juice 200 to 10,000 mg of hesperidin was added to 1000 ml of an apple or grape juice to obtain a health-improving fruit juice.

(3) Preparation of carbonated drink 20 to 10,000 mg of hesperidin was added to 1000 ml of Coca Cola® and Pepsi Cola® to obtain a health-improving carbonated juice.

EXAMPLE 8

Health foods containing Bioflavonoids (1) A health food was prepared by mixing the following ingredients and tableting the mixture.

|  | Quantity (wt/wt %) |
| --- | --- |
| Naringin, hesperidin or a plant extract containing it | 5 |
| Ginseng powder or extract | 20 |
| Sweetner and flavour | 75 |
| Total | 100 |

(2) Prepartion of buckwheat powder and Extraction of rutin from buckwheat

Buckwheat seeds, leaves, stems and flowers were dried at a room temperature and then powdered.

Alternatively, 100 g each of buckwheat leaves and flowers was extracted twice with 200 ml each of 70% ethanol at 40° C. for 5 hours. The extracts thus obtained were filtered. The resulting extracts had 1.8% and 4% of rutin, respectively.

In addition, $Ca(OH)_2$ was added to buckwheat leaves or flowers to pH 12.0 and the mixture was allowed to stand overnight. The mixture was adjusted to pH 6 to 7 and the resulting precipitate was recovered to obtain a crude rutin (purity: 40 to 50%).

A medicine or health food containing the rutin powder or extract thus obtained may be prepared in accordance with a conventional method.

(3) A mixture containing the following ingredients was prepared:

|  | Quantity (wt/wt %) |
| --- | --- |
| Onion powder | 40 |
| Garlic powder | 10 |
| Jujube powder | 30 |
| Buckwheat flower powder | 5 |
| Dry grape powder | 15 |
| Total | 100 |

The mixture was added to a conventional fodder in an amount of 5 wt % and the resulting fodder was fed to rats for 2 months. Consequently, the plasma HDL level of rats after 2 months increased by 30% as average in comparison with that of rats just before the administration.

While the invention has been described with respect to the above specific embodiments, it should be recognized that various modifications and changes may be made to the invention by those skilled in the art which also fall within the scope of the invention as defined by the appended claims.

What is claimed is:

1. A method for increasing the plasma high density lipoprotein(HDL) level in a mammal having low plasma HDL level which comprises administering an effective amount of a bioflavonoid of formula(I) or a plant extract containing same thereto:

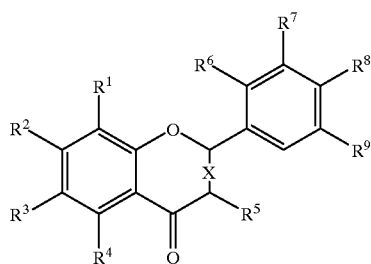

(I)

wherein, $R^1$, $R^2$, $R^3$, $R^4$, $R^5$, $R^6$, $R^7$, $R^8$ and $R^9$ are each independently hydrogen; a hydroxy group; a $C_{1-9}$ alkoxy group optionally substituted with one or more substituents selected from the group consisting of a hydroxy, $C_{1-3}$ alkoxy, aryloxy, and phenyl group substituted with 1 to 3 substituents selected from the group consisting of a hydroxy, alkoxy, aryloxy, halogen, nitro and amido group; a $C_{5-9}$ cycloalkyloxy group substituted with 1 to 3 substituents selected from the group consisting of a hydroxy, alkoxy, aryloxy, halogen, nitro and amido group; a $C_{5-9}$ cycloalkylcarbonyloxy group substituted with 1 to 3 substituents selected from the group consisting of a hydroxy, alkoxy, aryloxy, halogen, nitro and amido group; a $C_{2-10}$ or $C_{16-18}$ acyloxy group optionally substituted with one or more substituents selected from the group consisting of a hydroxy, $C_{1-5}$ alkoxy, aryloxy, and phenyl group substituted with 1 to 3 substituents selected from the group consisting of a hydroxy, alkoxy, aryloxy, halogen and nitro group; a rutinosyl group; or a rhaminosyl group; and X is a single or double bond.

2. The method of claim 1, wherein the mammal is human.

3. The method of claim 2, wherein the effective amount of the bioflavonoid ranges from 0.5 to 100 mg/kg body weight/day.

4. The method of claim 1, wherein the bioflavonoid is hesperidin, hesperetin, naringin, naringenin, diosmin, rutin, quercetin or a mixture thereof.

5. The method of claim 1, wherein the plant extract is a vegetable or fruit extract.

6. The method of claim 5, wherein the plant extract is an extract of buckwheat sprouts, seeds, leaves, stems or flowers.

7. The method of claim 1, wherein the bioflavonoid or plant extract is administered in the form of a pharmaceutical composition.

8. The method of claim 1, wherein the bioflavonoid or plant extract is administered in the form of an additive or a dietary supplement in food or beverage.

9. The method of claim 8, wherein the content of the bioflavonoid in the food ranges from 0.01 to 50% by weight.

10. The method of claim 8, wherein the content of the bioflavonoid in the beverage ranges from 200 to 10,000 mg per 1,000 ml of the beverage.

11. A method for increasing the plasma HDL level in a mammal having low plasma HDL level which comprises administering an effective amount of neohesperidin dihydrochalcone of formula(II) thereto:

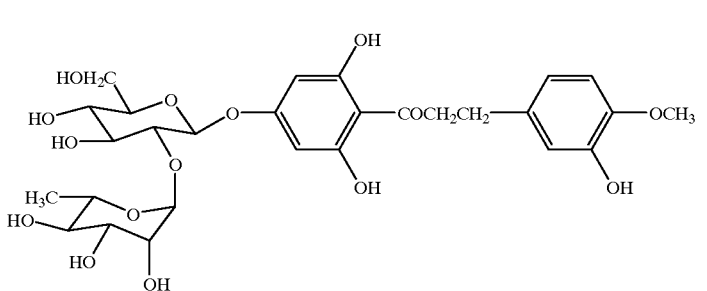

(II)

* * * * *